(12) United States Patent
Andrian et al.

(10) Patent No.: US 11,819,777 B2
(45) Date of Patent: Nov. 21, 2023

(54) SYSTEMS AND METHODS FOR ENHANCING AMINE AGENT RECOVERY WITH A RECLAIMER

(71) Applicant: Saudi Arabian Oil Company, Dhahran (SA)

(72) Inventors: Diki Andrian, Ras Tanura (SA); Amjad A. Alshaer, Qatif (SA)

(73) Assignee: SAUDI ARABIAN OIL COMPANY, Dhahran (SA)

( * ) Notice: Subject to any disclaimer, the term of this patent is extended or adjusted under 35 U.S.C. 154(b) by 620 days.

(21) Appl. No.: 15/683,548

(22) Filed: Aug. 22, 2017

(65) Prior Publication Data

US 2019/0060779 A1 Feb. 28, 2019

(51) Int. Cl.
*B01D 1/00* (2006.01)
*B01D 53/96* (2006.01)
(Continued)

(52) U.S. Cl.
CPC ....... *B01D 1/0082* (2013.01); *B01D 53/1425* (2013.01); *B01D 53/96* (2013.01); *F22D 1/12* (2013.01); *G05D 9/12* (2013.01); *G05D 23/00* (2013.01); *B01D 53/1456* (2013.01); *B01D 53/1475* (2013.01); *B01D 53/1493* (2013.01);
(Continued)

(58) Field of Classification Search
None
See application file for complete search history.

(56) References Cited

U.S. PATENT DOCUMENTS

| 2,914,469 A | * | 11/1959 | Draemel | B01D 53/1468 |
| | | | | 208/236 |
| 5,102,805 A | * | 4/1992 | Baughman | G01N 33/0013 |
| | | | | 423/229 |

(Continued)

FOREIGN PATENT DOCUMENTS

| JP | 2015097982 A | * | 5/2015 | ............. Y02C 10/06 |
| WO | WO-2007/146612 A2 | | 12/2007 | |
| WO | WO-2016/072292 A1 | | 5/2016 | |

OTHER PUBLICATIONS

Mitra, "A Technical Report on Gas Sweetening by Amines," ResearchGate, Jun. 29, 2015, 58 pages. (Year: 2015).*

(Continued)

*Primary Examiner* — Patrick Orme
(74) *Attorney, Agent, or Firm* — Osha Bergman Watanabe & Burton LLP

(57) ABSTRACT

Reclaimer systems and methods of their use are provided. Reclaimer systems use one or more fluid input streams and a variable steam input to control temperature of a fluid in a reclaimer vessel. In certain embodiments, a temperature controller and level controller are both connected to at least one fluid input stream subsystem and a steam input subsystem. Output from the level controller and the temperature controller is used to control flow through both a fluid input stream subsystem and a steam input subsystem. In certain embodiments, selectors are used to determine which controller output to obey when controlling the steam input subsystem and the fluid input stream subsystem. In certain embodiments, lean amine agent and an inert fluid are input in a ratio controlled by a ratio controller in order to maintain the fluid level in a vessel.

22 Claims, 3 Drawing Sheets

(51) Int. Cl.
*F22D 1/12* (2006.01)
*G05D 9/12* (2006.01)
*G05D 23/00* (2006.01)
*B01D 53/14* (2006.01)
*C07C 211/03* (2006.01)

(52) U.S. Cl.
CPC .......... *B01D 2252/204* (2013.01); *B01D 2252/20405* (2013.01); *B01D 2252/20421* (2013.01); *B01D 2252/20426* (2013.01); *B01D 2252/20431* (2013.01); *B01D 2252/20447* (2013.01); *B01D 2252/20478* (2013.01); *B01D 2257/304* (2013.01); *B01D 2257/308* (2013.01); *B01D 2257/502* (2013.01); *B01D 2257/504* (2013.01); *C07C 211/03* (2013.01)

(56) References Cited

U.S. PATENT DOCUMENTS

| | | | |
|---|---|---|---|
| 5,766,548 | A | 6/1998 | Soria |
| 5,993,608 | A | 11/1999 | Abry et al. |
| 8,425,849 | B2 | 4/2013 | Iijima et al. |
| 8,921,601 | B2 | 12/2014 | Millard |
| 9,623,366 | B2 | 4/2017 | Tsujiuchi et al. |
| 2013/0315809 | A1* | 11/2013 | Shimamura ........ B01D 53/1475 423/228 |
| 2014/0013945 | A1 | 1/2014 | Tanaka et al. |
| 2015/0083576 | A1 | 3/2015 | Aboudheir et al. |
| 2016/0256825 | A1* | 9/2016 | Tanaka ................ B01D 53/62 |
| 2016/0288049 | A1 | 10/2016 | Tanaka et al. |
| 2017/0291138 | A1 | 10/2017 | Tanaka et al. |

OTHER PUBLICATIONS

Merriam-Webster Dictionary, "Actuator," Merriam-Webster.com Dictionary, Merriam-Webster, accessed at https://www.merriam-webster.com/dictionary/actuator, on Mar. 14, 2022, 1 page. (Year: 2022).*
Huntsman Corporation, Diglycolamine® Agent—DGAR Agent Reclaimer Design and Operations, 5 pages, URL: www.huntsmangastreating.com (2006).
Wang, T. et al., Amine reclaiming technologies in post-combustion carbon dioxide capture, Journal of Environmental Sciences, 27: 276-289 (2015).
Coughran, M. et al., Jacketed Heating, Improve Batch Reactor Temperature Control; Rethink Reactor Temperature Control; Keep Cool When Designing Batch Reactors; Consider Hot Water For Jacketed Heating, 25 pages, (Dec. 31, 2010). URL: https://www.chemicalprocessing.com/assets/wp_downloads/pdf/CP1303-PickHeaters-jacketed-heating-final.pdf [Retrieved Nov. 8, 2018].
International Search Report for PCT/IB2018/055984, 5 pages (dated Nov. 29, 2018).
Kendall, D.C. et al., Process Control and Optimization, vol. 2, Instrument Engineers' Handbook, Fourth Edition, Chemical Reactors: Basic Control Strategies, 8.9: pp. 1664-1696, Chiller Optimization, 8.13: pp. 1729-1752 (Jan. 1, 2000).
Mitra, S., A Technical Report on Gas Sweetening by Amines, Research Gate, 58 pages (Jun. 29, 2015). URL: https://www.researchgate.net/publication/279298133 [Retrieved Nov. 8, 2018].
Sutter, P., Direct Steam Injection Hot Water Systems for Jacketed Heating, Pick Heaters Inc., 6 pages (Dec. 31, 2010). URL: http://www.pickheaters.com/Articles/DSI_Hot_Water_Systems_for_Jacketed_Heating.pdf [Retrieved on Nov. 8, 2018].
Written Opinion for PCT/IB2018/055984, 10 pages (dated Nov. 29, 2018).
Office Action Issued in Corresponding Chinese Application No. 2018800543536, dated Feb. 17, 2023, 19 pages.

* cited by examiner

SYSTEMS AND METHODS FOR ENHANCING AMINE AGENT RECOVERY WITH A RECLAIMER

TECHNICAL FIELD

The present application relates generally to systems for use in reclaiming amine agents and methods of their use.

BACKGROUND

Amine agents are used to remove certain undesirable gases from a gas stream. For example, amine agents are used to remove acid gases during gas sweetening processes. Amine agents are also used to scrub $CO_2$ from flue gas in post combustion capture processes. A reclaimer is used to reclaim useable amine agent from degradation products formed from amine agents during a gas removal process. Reclaimers generally utilize distillation processes to extract useable amine agent. Reclaimers are operated at an elevated temperature in order to produce sufficient evaporation of amine agent during the operational cycle. The efficiency of reclaiming amine agent is reduced or even totally inhibited at lower temperatures, for example, due to reduced evaporation of reclaimed amine agent. However, many amine agents will experience irreversible thermal degradation at high temperatures that exceed a certain threshold, thereby causing significant losses of amine agent. As amine agents are generally expensive, minimizing losses is important, and from a manufacturing process standpoint it is desirable to reduce the formation of degradation byproducts. Therefore, stable temperature control of a reclaimer is critical to reduce amine agent losses while maximizing the amount amine agent reclaimed in an operational cycle.

SUMMARY

Conventional reclaimer systems utilize a simple temperature control system to maintain the temperature of fluid in the reclaimer during its operation. A constant steam input is used to heat the fluid to the desired operational temperature. In order to prevent the steam from overheating the fluid (i.e., above the desired operational temperature), a water input stream connected to an independent temperature controller is provided. As temperature increases above the desired temperature, additional water provided by the input stream reduces the temperature of the fluid. An independent level controller is used to control flow of a lean amine agent into the reclaimer throughout the process in order to maintain the appropriate fluid level in the reclaimer and reclaim additional useable amine agent from the existing lean amine agent. However, the disclosure encompasses the recognition that in such conventional reclaimer systems independent control subsystems, the temperature of the fluid in the reclaimer system varies significantly above and below the desired operational temperature of the reclaimer during an operational cycle at least in part due to constant steam input and high degradation product concentration that occurs during operation. This variation in temperature both reduces the amount of amine agent reclaimed (when the temperature varies below the desired operational temperature) and increases amine agent losses due to irreversible thermal degradation (when the temperature varies above the desired operational temperature). Thus, there is a continued need for systems and methods to reduce amine agent losses during reclaiming and a previously unrecognized need for systems and methods that improve the temperature stability of fluid by using variable steam input in a reclaimer during operation.

Provided herein are systems for reclaiming amine agent from a lean amine agent input with a reclaimer that improve the temperature stability of fluid in a reclaimer while reclaiming the amine agent. Also provided are methods of use for such systems. Systems comprise one or more fluid input stream subsystems and a variable steam input subsystem that are both used to control the temperature of fluid in a reclaimer vessel. In certain embodiments, a temperature controller and level controller of the system are connected to (i) at least one of the one or more fluid input stream subsystems and (ii) a variable steam input subsystem. One or more selectors can be used in conjunction with a level controller and temperature controller in order to control the flow through at least one of the one or more fluid input stream subsystems and variable steam input subsystem. By controlling both flow of steam and the at least one fluid input stream into the vessel, a desired operational temperature can be stably maintained. In certain embodiments, the one or more fluid input stream subsystems comprises a lean amine agent input subsystem and a water input subsystem, which are connected by a ratio controller in order to dilute the lean amine agent input stream entering the vessel to enhance evaporation of reclaimed amine agent during operation.

Systems and methods disclosed herein can achieve higher amine agent recovery as compared to conventional reclaimer setups and further, in certain embodiments, do not require additional hardware or capital costs as compared to conventional reclaimer setups. That is, in certain embodiments, existing reclaimer systems comprising a temperature controller and level controller can be reconfigured to operate in accordance with the systems and methods disclosed herein by connecting the existing temperature controller and the existing level controller with both the existing steam input subsystem and the existing one or more fluid input stream subsystems. The existing temperature controller and the existing level controller may be reconfigured to be connected to the subsystems through at least one of one or more intermediate transfer functions, one or more intermediate controllers, and one or more selectors. Such additional controllers, transfer functions, and selectors are only programmable elements and thus do not necessarily require additional hardware in order to be added to a reclaimer system. Alternative systems that have been developed to improve amine agent recovery may require additional or different hardware beyond what is in a typical reclaimer system, resulting in high capital and implementation costs. Such alternative systems include systems that use vacuum pumps or multi-stage reclaimers.

In certain embodiments, the disclosed technology includes a method for reclaiming one or more amine agents, the method comprising: controlling temperature of a fluid in a vessel (e.g., a horizontal or vertical reclaimer), at least in part, by providing one or more fluid input streams (e.g., wherein at least one of the one or more fluid input streams comprises water (e.g., reflux water)) and providing a variable steam input to the vessel (e.g., wherein the steam is in indirect contact with the fluid such that at least some energy from the steam is transferred from the steam to the fluid), wherein the fluid comprises one or more degradation products that have been formed from reaction of the one or more amine agents with one or more gases (e.g., one or more acid gases (e.g., wherein the one or more acid gases comprises at least one of $CO_2$, COS, CO, $H_2S$, and $CS_2$)).

In certain embodiments, a method comprises decreasing, increasing, or both decreasing and increasing the temperature of the fluid, during a period of time, in order to maintain the temperature at a desired temperature or within a desired temperature range, thereby inhibiting thermal degradation of the one or more amine agents during the period of time (e.g., wherein the desired temperature or desired temperature range has been determined based on thermal degradation temperature(s) of at least one of the one or more amine agents).

In certain embodiments, temperature is maintained within 5% (e.g., 3%, 2%, 1%, 0.75%, 0.5%, or 0.2%) of the desired temperature or bounds of the desired temperature range. In certain embodiments, temperature of the fluid is either increased or decreased based, at least in part, on an output of a temperature controller and an output of a level controller.

In certain embodiments, a method comprises receiving a first high selector input into a high selector, wherein the first input is based on the output of the temperature controller; receiving a second high selector input into the high selector, wherein the second input is based on the output of the level controller; determining whether the first high selector input or the second high selector input is higher; and altering flow of the one or more fluid input streams based on the determination. In certain embodiments, a method comprises receiving a first low selector input into a low selector, wherein the first input is based on the output of the temperature controller; receiving a second low selector input into the low selector, wherein the second input is based on the output of the level controller; determining, using the low selector, whether the first low selector input or the second low selector input is lower; and altering the variable steam input provided based on the determination. In certain embodiments, at least one of output of the temperature controller and output of the level controller is an input of a transfer function.

In certain embodiments, one or more fluid input streams comprises a lean amine agent input stream and a water input stream (e.g., a reflux water input stream).

In certain embodiments, a method comprises providing the lean amine agent input stream and the water input stream in a ratio controlled by a ratio controller in order to increase a level of the fluid in the vessel. In certain embodiments, providing the lean amine agent input stream and the water input stream in the ratio reduces concentration of the one or more degradation products in the fluid in the vessel (e.g., reduces boiling point of the fluid in the vessel).

In certain embodiments, the disclosed technology includes a method for controlling temperature of a fluid in a vessel in order to reclaim one or more amine agents, the method comprising: controlling input of one or more fluid input streams into the vessel based on output of a first selector (e.g., a high selector) that receives input, directly or indirectly, from a level controller and a temperature controller (e.g., wherein at least one of the one or more fluid input streams comprises water (e.g., reflux water)); and controlling variable input of steam to the vessel based on output of a second selector (e.g., a low selector) that receives input, directly or indirectly, from the level controller and the temperature controller (e.g., wherein the steam is in indirect contact with the fluid such that at least some energy from the steam is transferred from the steam to the fluid), (e.g., wherein the fluid comprises one or more degradation products that have been formed from reaction of the one or more amine agents with one or more gases (e.g., one or more acid gases (e.g., wherein the one or more acid gases comprises at least one of $CO_2$, COS, CO, $H_2S$, and $CS_2$))).

In certain embodiments, a method comprises decreasing, increasing, or both decreasing and increasing the temperature of the fluid, during a period of time, in order to maintain the temperature at a desired temperature or within a desired temperature range, in order to inhibit thermal degradation of the one or more amine agents during the period of time (e.g., wherein the desired temperature or desired temperature range has been determined based on thermal degradation temperature(s) of at least one of the one or more amine agents). In certain embodiments, the temperature is maintained within 5% (e.g., 3%, 2%, 1%, 0.75%, 0.5%, or 0.2%) of the desired temperature or bounds of the desired temperature range.

In certain embodiments, at least one output of the temperature controller and the level controller is an input of a transfer function. In certain embodiments, the one or more fluid input streams comprises a lean amine agent input stream and a water input stream (e.g., a reflux water input stream).

In certain embodiments, a method comprises providing the lean amine agent input stream and the water input stream in a ratio controlled by a ratio controller in order to increase a level of the fluid in the vessel. In certain embodiments, providing the lean amine agent input stream and the water input stream in the ratio reduces concentration of the one or more degradation products in the fluid in the vessel (e.g., reduces boiling point of the fluid in the vessel).

In certain embodiments, the disclosed technology includes a system for reclaiming one or more amine agents, the system comprising: a vessel; a temperature controller; a level controller; a steam input subsystem, wherein steam input through the steam input subsystem provides energy into fluid in the vessel; and one or more fluid input stream subsystems (e.g., a water (e.g., reflux water) input subsystem and a lean amine agent input subsystem) for providing one or more fluid input streams into the vessel, wherein the temperature controller and the level controller are both connected to both the steam input subsystem and the water input subsystem such that temperature of fluid in the vessel is controlled, at least in part, by the water input subsystem and the steam input subsystem.

In certain embodiments, a system comprises a high selector, wherein the high selector receives one or more inputs based on an output of the temperature controller and an output of the level controller and an output of the high selector is used to control flow through the one or more fluid input stream subsystems. In certain embodiments, a system comprises a low selector, wherein the low selector receives one or more inputs based on an output of the temperature controller and an output of the level controller and an output of the high selector is used to control flow of steam through the steam input subsystem. In certain embodiments, one or more transfer functions, wherein each of the one or more transfer functions modifies an output of one of the level controller or the temperature controller and the output of each of the one or more transfer functions is an input of a high selector. In certain embodiments, a system comprises one or more transfer functions, wherein each of the one or more transfer functions modifies an output of one of the level controller or the temperature controller and the output of each of the one or more transfer functions is an input of a low selector.

In certain embodiments, the one or more fluid input streams of a system comprises: a lean amine agent input subsystem, wherein lean amine agent flows into the vessel through the lean amine agent input subsystem, and a water (e.g., reflux water) input subsystem for providing water into the vessel; and the system comprises: a ratio controller connected to the lean amine agent input subsystem and the water input subsystem, wherein the ratio controller controls a ratio of lean amine agent and water that flows into the vessel. In certain embodiments, lean amine agent and water provided to the vessel in the ratio reduces concentration of the one or more degradation products in the fluid in the vessel is reduced (e.g., boiling point of the fluid in the vessel is reduced).

In certain embodiments, at least the temperature controller and level controller are configured to cause temperature of a fluid in the vessel to be decreased, increased, or both, during a period of time, in order to maintain the temperature at a desired temperature or within a desired temperature range, in order to inhibit thermal degradation of the one or more amine agents during the period of time (e.g., wherein the desired temperature or desired temperature range has been determined based on thermal degradation temperature(s) of at least one of the one or more amine agents). In certain embodiments, the temperature is maintained within 5% (e.g., 3%, 2%, 1%, 0.75%, 0.5%, or 0.2%) of the desired temperature or bounds of the desired temperature range.

In certain embodiments, the system is configured to supply a variable steam input through the steam input subsystem.

In certain embodiments of systems and methods disclosed herein, the one or more amine agents comprises at least one of a primary amine, a secondary amine, and a tertiary amine. In certain embodiments of systems and methods disclosed herein, the one or more amine agents comprises at least one of diglycolamine (DGA), monoethanolamine (MEA), diethanolamine (DEA), diisopropanolamine (DIPA), triethanolamine (TEA), methyldiethanolamine (MDEA), 2-amino-2-methyl-1-propanol (AMP), and piperazine (PZ). In certain embodiments of systems and methods disclosed herein, the one or more amine agents comprises diglycolamine (DGA) and the temperature of the fluid is decreased, increased, or both, during the period of time, in order to maintain the temperature within between about 355° F. and about 365° F. (e.g., between about 358° F. and about 362° F.). In certain embodiments of systems and methods disclosed herein, the one or more amine agents consists of DGA. In certain embodiments of systems and methods disclosed herein, the temperature of the fluid is decreased, increased, or both, during the period of time, in order to maintain the temperature within between about 355° F. and about 365° F. (e.g., between about 358° F. and about 362° F.). In certain embodiments of systems and methods disclosed herein, the temperature is maintained at about 360° F. (e.g., within 0.75%, 0.5%, or 0.2% of 360° F.). In certain embodiments of systems and methods disclosed herein, the vessel is a conventional horizontal kettle reclaimer (e.g., with a L/D ratio of 2-5).

Definitions

As used in this application, the term "comprise" and variations of the term, such as "comprising" and "comprises," are not intended to exclude other additives, components, integers or steps. As used in this application, the terms "about" and "approximately" are used as equivalents. Any numerals used in this application with or without about/approximately are meant to cover any normal fluctuations appreciated by one of ordinary skill in the relevant art. In certain embodiments, the term "approximately" or "about" refers to a range of values that fall within 3%, 2%, 1%, 0.75%, 0.5%, 0.25% or less in either direction (greater than or less than) of the stated reference value unless otherwise stated or otherwise evident from the context.

Amine agent: As used herein, the term "amine agent" refers to a chemical species comprising an amine functional group. An amine agent can be a primary amine, secondary amine, or tertiary amine, or a combination thereof. Amine agents can be a cyclic diamine. Amine agents may be an alkanolamine. Amine agents suitable for use with the methods and systems disclosed herein include, but are not limited to, diglycolamine (DGA), monoethanolamine (MEA), diethanolamine (DEA), diisopropanolamine (DIPA), triethanolamine (TEA), methyldiethanolamine (MDEA), 2-amino-2-methyl-1-propanol (AMP), and piperazine (PZ). One or more amine agents may be used in a single process (e.g., gas sweetening process) such that at least some of each of the one or more amine agents is reclaimed with a reclaimer.

Lean amine agent: As used herein, the term "lean amine agent" is used as is conventional in the art when referring to reclaimers. Namely, "lean amine agent" refers to an amine agent fluid comprising at least some amount of one or more degradation products formed from a reaction of an amine agent with another species. Lean amine agent can further comprise another solvent or species, such as water.

Degradation product: As used herein, the term "degradation product" refers to chemical species that form from reaction with an amine agent. It will be appreciated that degradation products as a term of art includes, for example, both products of a reaction of an amine agent and another species during gas sweetening (e.g., BHEEU), as well as thermal degradant byproducts that may form during reclamation of amines (e.g., morpholine). Degradation products may reversibly or irreversibly formed. As used herein, heat stable salts (HSSs) that comprise degraded amine agents are degradation products.

Operational Cycle: As used herein, the term "operational cycle" is used to refer to the period of time a reclaimer is actively being used to reclaim useable amine agent from degradation products in a lean amine agent input stream. The operational cycle starts when a reclaimer vessel is initially filled with fluid and ends when the reclaimer vessel is flushed to remove byproducts accumulated in the bottom of the reclaimer vessel since the vessel was initially filled with fluid.

Desired temperature and desired operational temperature: As used herein, the terms "desired temperature" and "desired operational temperature" are used interchangeably to refer to a pre-selected temperature at which a reclaimer system is configured to operate. In some embodiments, there is a plurality of desired operational temperatures such that a desired operational temperature range exists. Generally, the desired temperature for a reclaimer system or method of its use depends on the amine agent being used. The desired operational temperature for a reclaimer system or method may be selected in order to limit irreversible thermal degradation of an amine agent below a threshold rate of thermal degradation. For example, in certain embodiments, when a system or method uses DGA as its sole amine agent, the desired temperature is 360 degrees Fahrenheit (° F.), the temperature above which DGA appreciably thermally degrades to morpholine. In certain embodiments, a desired temperature is used as a temperature setpoint for a reclaimer system.

Inert fluid: As used herein, the term "inert fluid" refers to a fluid that acts as a solvent during operation of a reclaimer system. An inert fluid input can be used to cool fluid in a reclaimer vessel. An inert fluid input can be used to dilute degradation products in a reclaimer vessel. In certain embodiments, water is used as an inert fluid. In certain embodiments, reflux water is used as an inert fluid.

BRIEF DESCRIPTION OF THE DRAWING

Drawings are presented herein for illustration purposes, not for limitation. The foregoing and other objects, aspects, features, and advantages of the disclosure will become more apparent and may be better understood by referring to the following description taken in conjunction with the accompanying drawings, in which.

DETAILED DESCRIPTION

It is contemplated that systems, devices, methods, and processes of the disclosure encompass variations and adaptations developed using information from the embodiments described herein. Adaptation and/or modification of the systems, devices, methods, and processes described herein may be performed by those of ordinary skill in the relevant art.

Throughout the description, where articles, devices, and systems are described as having, including, or comprising specific components, or where processes and methods are described as having, including, or comprising specific steps, it is contemplated that, additionally, there are articles, devices, and systems of the present disclosure that consist essentially of, or consist of, the recited components, and that there are processes and methods according to the present disclosure that consist essentially of, or consist of, the recited processing steps.

It should be understood that the order of steps or order for performing certain action is immaterial so long as operability is not lost. Moreover, two or more steps or actions may be conducted simultaneously.

Conventional reclaimer systems utilize independent subsystems for controlling fluid temperature and fluid level in the reclaimer during an operational cycle. The temperature and level are maintained such that reflux water and reclaimed amine agent are continuously evaporated and removed from the reclaimer in a distillation process throughout an operational cycle of the reclaimer. Constant steam input is used to heat the fluid to a desired operational temperature. Variable reflux water input is used to prevent excessive overheating of the fluid. Lean amine agent input is used to increase the fluid level to ensure proper operation of the reclaimer throughout a cycle. Additional lean amine agent input further provides additional amine agent degradation products to be reclaimed into useable amine agent. In this way, additional lean amine agent is input into a reclaimer vessel periodically overtime as the fluid level falls too low resulting in additional reclaimed amine agent being extracted from the reclaimer. After a full operational cycle, an amount of byproducts (including at least one of solids, sludge, heat stable salts, decomposition and degradation products) remain in the reclaimer and are flushed from the system prior to starting a new operational cycle.

Figure 1:
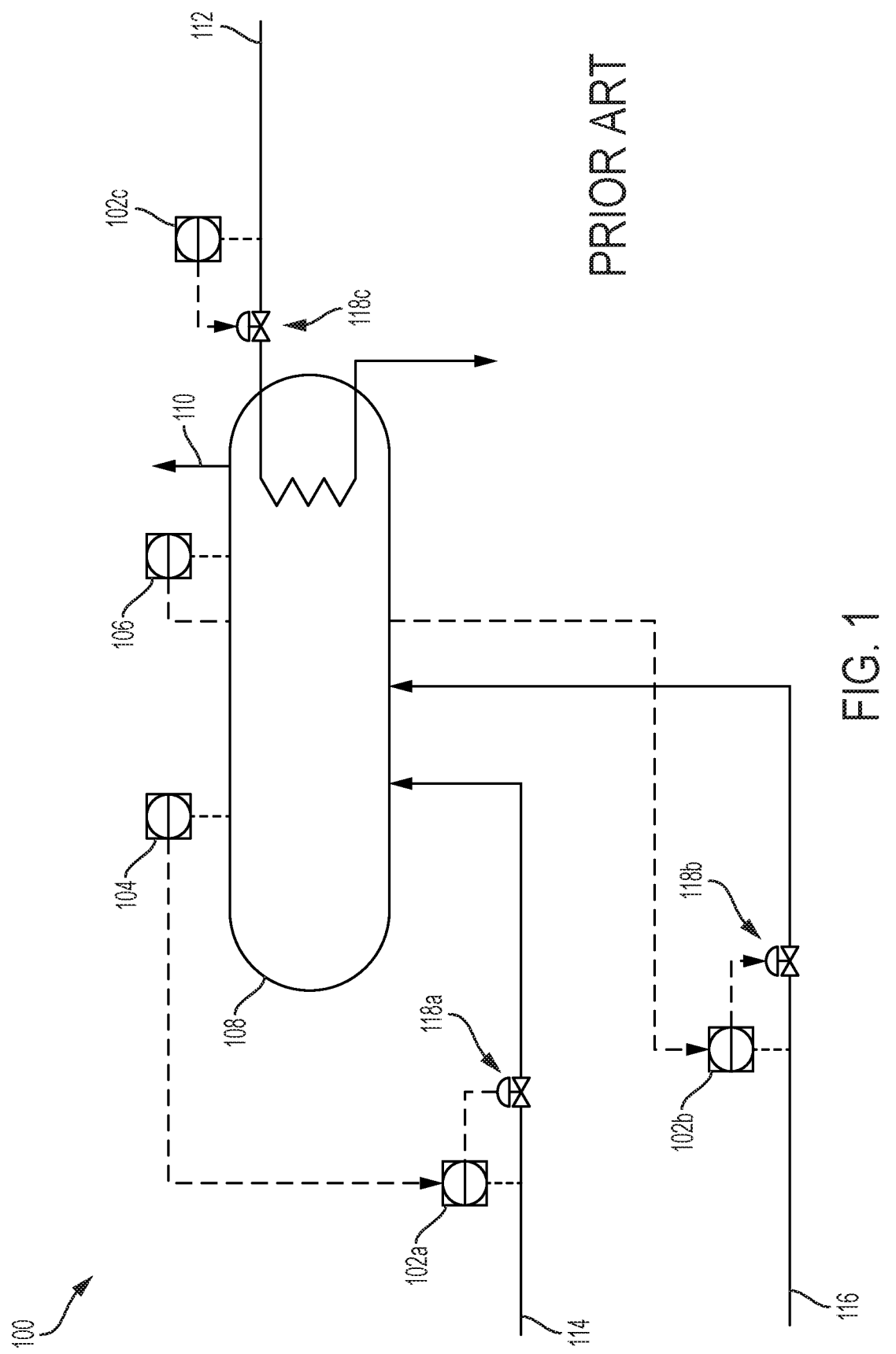
FIG. 1 is a process flow diagram for an exemplary conventional reclaimer system.

FIG. 1 is a process flow diagram for an exemplary conventional reclaimer system 100. Such conventional reclaimer systems are used as part of many gas sweetening systems currently in operation throughout the world. The fluid from which amine agent is reclaimed in system 100 is contained in vessel 108. During operation, in order to heat the fluid to the desired operational temperature, steam is input to vessel 108 using steam input subsystem 112. Steam flows through subsystem 112 into vessel 108 where it is in indirect contact with fluid in the vessel. Steam input subsystem 112 may include one or more tube bundles through which the steam flows that are in contact with fluid in the vessel 108. Alternatively, steam may be input directly into a vessel. Steam input subsystem 112 comprises flow indicator and controller (FIC) 102c and control valve 118c and is configured to provide a constant input of steam during operation. Steam flow rate and steam temperature are predetermined based on the desired operational temperature of a reclaimer system.

Temperature controller 106 is connected to reflux water input subsystem 102b. Reflux water input subsystem 116 comprises FIC 102b and control valve 118b that collectively control the flow of reflux water through the subsystem into vessel 108 based on output from temperature controller 106. As such, when temperature controller 106 registers that the fluid temperature is above its setpoint (i.e., too high) in vessel 108, reflux water input subsystem 116 provides additional reflux water to cool the fluid by increasing or initiating reflux water flow through subsystem 116. As can be seen in FIG. 1, the steam flow from steam input subsystem 112 is independent of both temperature controller 106 and reflux water input subsystem 116. Increasing or decreasing water flow through the water flow subsystem is the only control mechanism used to control fluid temperature in the vessel in conventional reclaimer systems.

Level controller 104 is connected to lean amine agent input subsystem 114. When the level drops below its setpoint, additional lean amine agent is provided by lean amine agent input subsystem 104. Lean amine agent subsystem 114 comprises FIC 102a and control valve 118a that collectively control the flow of lean amine agent through the subsystem into vessel 108 based on the output of level controller 104. The setpoint can depend on the position of tube bundles in the reclaimer that provide heat from the flowing steam. The setpoint can depend on other considerations such as mass and heat balance within the interior chamber of the reclaimer vessel in order to optimize the reclaiming rate of lean amine agent.

Throughout operation of the reclaimer during an operational cycle, steam input constantly heats fluid in vessel 108, water input cools the fluid when needed, and lean amine agent input maintains the level at its setpoint. Water and amine agent vapors form due the elevated temperature and exit vessel 108 through outlet 110. Outlet 110 is located on the top of vessel 108 in order to allow the vapors to naturally escape. One or more other outlets with valves (not shown) may be disposed on the bottom of vessel 108 in order to allow residual byproducts to be flushed from the reclaimer at the end of an operational cycle.

Figure 2:
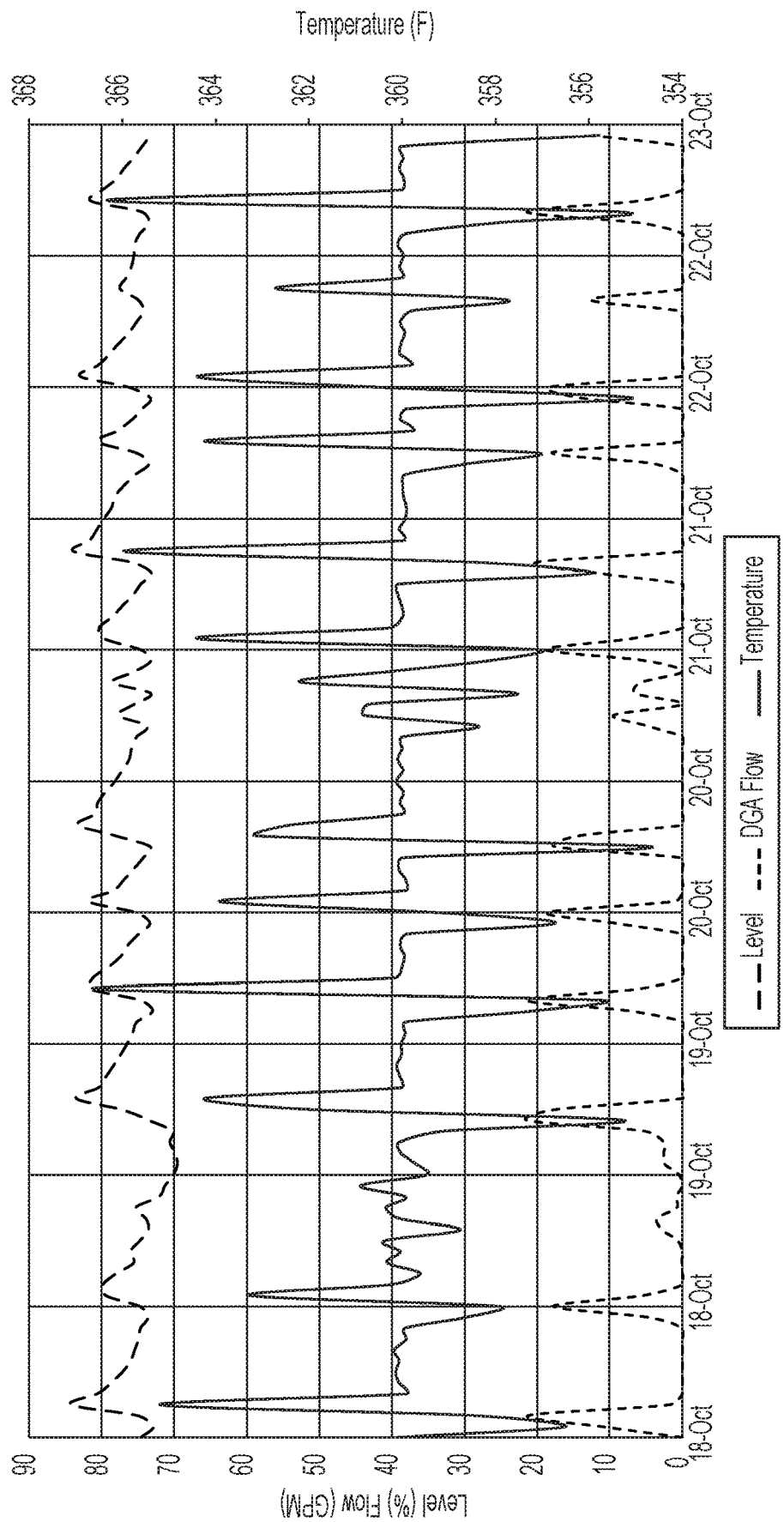
FIG. 2 is a plot that shows the significant variation in fluid temperature that occurs in a conventional reclaimer system.

FIG. 2 shows actual gas plant data for a reclaimer system that is arranged and functions in accordance with exemplary conventional reclaimer system 100. The amine agent used in the reclaimer system is DGA. As is known in the art, a desired operational temperature of a reclaimer used to reclaim DGA is 360° F. Above 360° F., irreversible thermal degradation of DGA to morpholine is appreciable. The data in FIG. 2 identify previously unrecognized problems with conventional reclaimer systems: the fluid level and fluid temperature vary widely throughout an operational cycle leading to suboptimal performance of conventional reclaimer systems at least in part due to constant steam input and high degradation product concentration that occurs during operation. Furthermore, FIG. 2 identifies that the lean amine flow rate (labeled "DGA Flow" in FIG. 2) is intermittent, which leads to variable properties of the fluid in the reclaimer vessel, such as viscosity.

As can be understood from FIG. 2, the lean amine flow to the reclaimer is intermittent and the fluid temperature varies significantly over time at least partially due to the intermittent lean amine flow. Lean amine flow has periods of relatively high flow followed by periods of little or no flow. This intermittent flow also causes the fluid level in the reclaimer vessel to vary around its setpoint. Furthermore, a variable flow rate of lean amine into a reclaimer results in a variable viscosity of the fluid in the vessel. When large volumes of lean amine agent are input into a reclaimer vessel, the concentration of degradation products (and consequently viscosity) increases sharply due to the degradation products present in the lean amine agent flow formed from reaction of the amine agent with one or more gases. The concentration of the degradation products in the lean amine agent flow depends on the concentration of reactive gases in a feed gas of the gas processing system that comprises the reclaimer vessel (e.g., sour gas in a sour gas sweetening system). During periods where no lean amine agent is input, concentration of degradation products and viscosity falls. Since boiling point varies directly with viscosity, the boiling point of the fluid varies due to the intermittent lean amine agent flow. When boiling point of the fluid increases, the evaporation rate of reclaimed amine agent in the reclaimer decreases to a suboptimal rate, consequently, lean amine flow goes to zero since level is higher than level control valve set point.

The average temperature of the reclaimer system over the period shown in FIG. 2 is approximately the desired operational temperature (e.g., the setpoint), but varies significantly between approximately 366° F. and approximately 355° F. Additional measurements (not shown in FIG. 2) demonstrate a full range of temperature variation between about 350° F. and about 370° F. When the temperature is at or near 370° F., the DGA amine agent appreciably thermally degrades to morpholine. When the temperature is at or near 350° F., reclaiming of DGA from degradation products (such as N,N'bis(hydroxyethoxyethyl) urea (BHEEU)) is significantly reduced. Thus, performance of the reclaimer system used to generate the data shown in FIG. 2 is suboptimal, incurring undesirable loss amine agent through thermal degradation and inefficient reclaiming of amine agent.

As discussed above, the present disclosure includes the previously unrecognized source of a problem regarding temperature control in amine agent reclamation systems that arises from constant steam input and high degradation product concentrations. The problems identified in conventional reclaimer systems, as described in the preceding paragraphs of Detailed Description, can be addressed, at least in part, with the systems and methods disclosed herein. Without wishing to be bound by any particular theory, it is believed that the sub-optimal performance of conventional reclaimer systems arises from the isolated control systems for lean amine agent input, water input, and the constant steam input. Constant steam input increases temperature of fluid in a reclaimer; intermittent water input decreases the temperature; and lean amine agent increases the fluid level. In contrast to conventional systems, systems and methods in accordance with the present disclosure use both variable steam input and variable inert fluid input to control temperature of a fluid in a reclaimer. In certain embodiments, systems have a connected control scheme wherein a level controller and temperature controller are both connected to the variable steam input and one or more fluid input streams that flow through their respective subsystems. In certain embodiments, temperature is increased or decreased, or both in order to maintain a desired operational temperature or stay within a desired temperature range. In certain embodiments, the desired operational temperature or desired temperature range depends on the one or more amine agents being used in a system.

In certain embodiments, fluid input stream subsystems include a subsystem for lean amine agent input and a subsystem for inert fluid input. In certain embodiments, a lean amine agent input and inert fluid input are provided to a reclaimer, when a level of the reclaimer is below a setpoint, in a ratio such that the level of fluid in a reclaimer vessel is maintained at the setpoint through addition of both lean amine agent and inert fluid. The use of both inert fluid and lean amine agent in a ratio allows a fluid level in a reclaimer to be maintained at a setpoint while diluting the concentration of degradation products in a reclaimer vessel. For example, lean amine agent can be input in a ratio, relative to inert fluid input, of 10:1 or less, 9:1 or less, 8:1 or less, 7:1 or less, 6:1 or less, 5:1 or less, 4:1 or less, or 3:1 or less. In certain embodiments, lean amine agent is input in a ratio, relative to inert fluid input, of about 10:1, about 9:1, about 8:1, about 7:1, about 6:1, about 5:1, about 4:1, or about 3:1. Increase in degradation product concentration can increase fluid viscosity in the vessel and consequently increase the boiling point of the fluid. In certain conventional systems, operational cycles are shortened due to such viscosity increases. Therefore, in certain embodiments of the presently disclosed systems and methods, viscosity and boiling point variabilities are reduced by diluting lean amine input with additional inert fluid input. Reduced variability optimizes evaporation of reclaimed amine agent and can allow use of longer operational cycles.

Systems and methods disclosed herein are used to increase and decrease temperature of a fluid in a reclaimer in multiple ways in order to maintain the temperature at a desired operational temperature (e.g., setpoint) or within a desired operational temperature range, thereby enhancing reclamation of amine agents while reducing amine agent loss, as compared to a conventional reclaimer system. Steam input through a steam input subsystem can be increased to increase temperature of a fluid in a vessel or decreased to decrease the temperature. Likewise, water flow can be increased to decrease the temperature or decreased to increase the temperature. In certain embodiments, when a level controller and temperature controller are included in a system and both connected to a steam input subsystem that controls steam input and an inert fluid subsystem that controls input of an inert fluid, outputs from a level controller and temperature controller are used to determine if temperature should be increased or decreased to maintain a setpoint (e.g., at a desired operational temperature) by controlling inert fluid input, steam input, or both. In certain embodiments, selectors are used to determine whether to obey input based on a level controller or input based on a temperature controller. Output from a selector may cause flow (e.g., inert fluid or steam flow) to be altered or to remain constant. One or more constant or variable transfer functions may be used to modify output of a controller prior to input into a selector, for example, in order to make a logical comparison of level controller output and temperature controller output. In certain embodiments, systems and methods disclosed herein offer more dynamic control of fluid level and fluid temperature in a reclaimer (as compared to a conventional reclaimer system), which results in increased temperature and level stability (i.e., reduced variability) during operation.

Systems and methods disclosed herein are used to convert degradation products reversibly formed from one or more amine agents into reclaimed, useable amine agent. Degradation products are formed from reaction of an amine agent with one or more gases. The one or more gases may comprise one or more acid gases. For example, the one or more gases may comprise at least one of $CO_2$, COS, CO, $H_2S$, and $CS_2$. One or more amine agents may be used in a single system. An amine agent being reclaimed using a reclaimer system or reclaiming method may be a primary amine, secondary amine, or tertiary amine. An amine agent may be a cyclic amine. An amine agent may be an alkanolamine. Amine agents suitable for use with the methods and systems disclosed herein include, but are not limited to, diglycolamine (DGA), monoethanolamine (MEA), diethanolamine (DEA), diisopropanolamine (DIPA), triethanolamine (TEA), methyldiethanolamine (MDEA), 2-amino-2-methyl-1-propanol (AMP), and piperazine (PZ). Systems and methods disclosed herein may be used for post-combustion capture, gas sweetening, or any other process wherein degradation products are formed from reactions with amine agents and amine agent losses are undesirable.

In order to minimize amine agent loss from irreversible thermal degradation while efficiently reclaiming amine agent from degradation products, systems (and methods) disclosed herein can be used (performed) at a desired operational temperature or within a desired operational range. That is, the temperature setpoint of a reclaimer system can be set to be a desired operational temperature (e.g., based on an amine agent being reclaimed with the system (during the method)). In certain embodiments, temperature of fluid in a reclaimer vessel in accordance with systems disclosed herein and operated in accordance with methods disclosed herein is maintained within 5% of a desired temperature. For example, temperature may be maintained within 3%, 2%, 1%, 0.75%, 0.5%, or 0.2% of the desired temperature. In certain embodiments, temperature of fluid in a reclaimer vessel in accordance with systems disclosed herein and operated in accordance with methods disclosed herein is maintained within 5% of a bounds of a desired temperature range. For example, temperature may be maintained within 3%, 2%, 1%, 0.75%, 0.5%, or 0.2% of the bounds of the desired temperature range. Thus, in certain embodiments, temperature stability is improved (variability is reduced).

Figure 3:
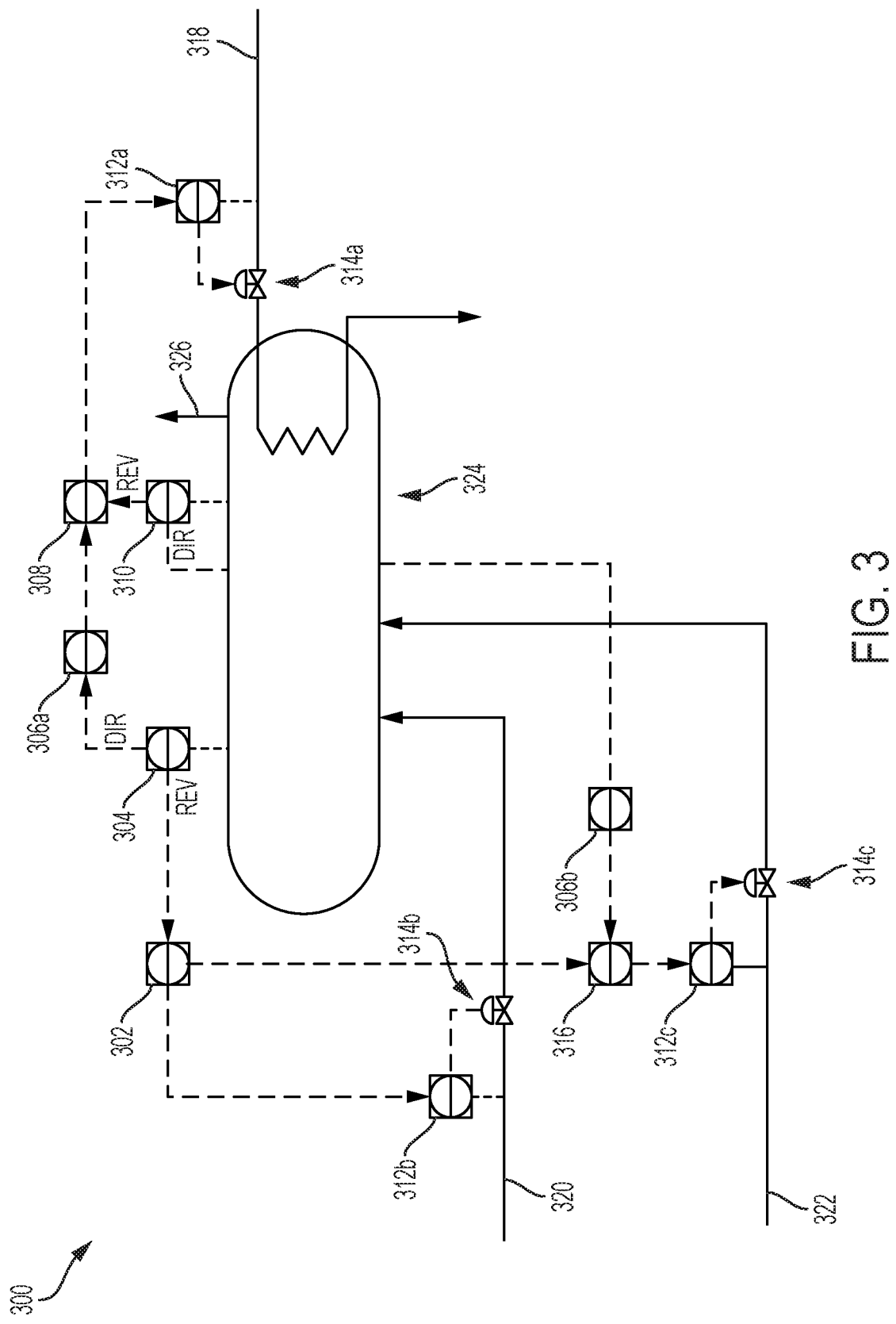
FIG. 3 is a process flow diagram for an exemplary reclaimer system with variable steam input, according to an illustrative embodiment of the disclosure.

FIG. 3 is a process flow diagram for exemplary reclaimer system 300, the reclaimer system of an illustrative embodiment of the systems and methods disclosed herein. Level controller 304 and temperature controller 310 monitor a level and temperature of fluid in vessel 324, respectively. Both level controller 304 and temperature controller 310 are connected to both variable steam input subsystem 318 and at least one of the fluid input stream subsystems (lean amine agent input subsystem 320 and water input subsystem 322). Flow through fluid input stream subsystems (320 and 322) and variable steam input subsystem 318 is controlled based, at least in part, on output from level controller 304 and temperature controller 310 (i.e., the fluid level and fluid temperature in vessel 324, respectively). Both temperature and level of fluid in vessel 324 can be maintained at their respective setpoints based on controlling fluid flow through subsystem 322 and steam flow through subsystem 318. Reclaimer systems may have other controllers whose output is used in controlling flow through one or more of the fluid input stream subsystems and the variable steam input subsystem in addition to or in place of the controllers shown in exemplary reclaimer system 300.

Variable steam input subsystem 318, lean amine agent input subsystem 320, and water input stream subsystem 322 each comprise an FIC (312a, 312b, and 312c, respectively) and a control valve (314a, 314b, and 314c, respectively). Together, the subsystems (318, 320, and 322) control the flow of fluids and steam into vessel 324. Steam input subsystem 318 and water input subsystem 322 are both indirectly connected to level controller 304 and temperature controller 310. Lean amine agent input subsystem 320 is connected to level controller 304 through ratio controller 302. The steam and input fluid stream subsystems (318, 320, and 322) are connected to vessel 324 with fittings such that fluid from the input fluid stream subsystems enters an interior chamber of vessel 324 and heat from the steam flowing through the steam input subsystem is provided to the interior chamber.

Steam flow through steam input subsystem 318 is variable and is based, at least in part, on output from temperature controller 310 and level controller 304. Steam flow through reclaimer systems disclosed herein is variable in that at least one of the temperature and flow rate of steam through the subsystem is varied by controlling input to a control valve of a steam input subsystem. Exemplary reclaimer system 300 uses a variable steam flow rate at constant input temperature. A steam input subsystem may comprise or be connected to one or more tube bundles disposed within a vessel. The one or more tube bundles may be any of those known in the art, disposed within the vessel in any conventional arrangement (i.e., such that fluid in the vessel covers the tubes while leaving sufficient room in the vessel for vapor above the upper fluid surface). Steam input into a vessel may be direct or indirect. By direct it is meant that the steam may enter the vessel to make direct contact with the fluid. By indirect it is meant that the steam may flow through one or more tube bundles or other such structures such that heat from the steam is transferred to fluid in a vessel without the steam directly contacting the fluid.

Water flow through water input subsystem 322 is variable and is based, at least in part, on output from temperature controller 310 and level controller 304. Water flows directly into vessel 324 to mix with fluid already in the vessel. Lean amine agent flow through lean amine agent input subsystem 320 is based, at least in part, on output from level controller 304. Lean amine agent flows directly into vessel 324 to mix with fluid already in the vessel.

Lean amine agent subsystem 320 and water input subsystem 322 are both connected to ratio controller 302. Ratio controller 302 is configured to provide lean amine agent flow and water flow to vessel 324 in a desired ratio when fluid level in reclaimer vessel 324 is below a setpoint. A desired ratio is selected or determined to control (e.g., dilute) the viscosity of fluid entering vessel 324 sufficiently, for example, in order to decrease a degradation product concentration in the vessel while maintaining a sufficient evaporation rate of reclaimed amine agent during operation. Ratio controller can be configured to provide a constant (e.g., predetermined) or variable ratio. A ratio controller configured with a variable ratio may have output that is determined based on properties of fluid in the vessel, such as viscosity, with the output changing over time as the fluid properties change. A ratio controller may be configured to provide a ratio depending on a measured or input (e.g., manually) concentration of degradation products in a lean amine agent stream. Decreasing the degradation product concentration in a vessel reduces the viscosity of fluid in the vessel and consequently reduces the boiling point of the fluid, thereby promoting an increased evaporation rate of reclaimed amine agent without increasing the temperature of fluid in the reclaimer vessel. Ratio controller 302 is directly connected to level controller 304. As indicated in FIG. 3, level controller 304 acts as a reverse-acting controller when providing output to ratio controller 302. Thus, when the level of fluid in vessel 324 falls below the setpoint, additional fluid will be provided to the vessel, wherein the additional fluid comprises both lean amine agent from lean amine agent subsystem 320 and water from water input subsystem 322 in a ratio controlled by ratio controller 302.

Lean amine agent subsystem 320 and water input subsystem 322 are shown to enter vessel 324 using separate fittings attached to the vessel. In certain embodiments, lean amine agent flowing through an lean amine agent subsystem and at least a portion of water flowing through a water input subsystem are mixed in a separate mixing vessel prior to being provided to the main reclaiming vessel. In certain embodiments, no ratio controller is included in a reclaimer system. In such embodiments, either (i) only lean amine agent is input (through a lean amine agent input subsystem) to increase fluid level in a reclaimer vessel or (ii) inert fluid and lean amine agent are both input without use of a controlled ratio. Water input subsystem 322 may use fresh water or reflux water. In certain embodiments, a reclaimer system comprises one or more fluid input stream subsystems that provide inert fluid(s) to a vessel in the reclaimer system in addition to or in place of a water input subsystem.

Steam input subsystem 318 is connected to low selector 308. Low selector 308 receives two inputs: output from temperature controller 310 and modified output from level controller 304. As indicated in FIG. 3, temperature controller 310 is configured to act as a reverse-acting controller when providing input to low selector 308. As indicated in FIG. 3, level controller 304 is configured to act as a direct-acting controller when providing output that is modified by transfer function 306a before being provided as input to low selector 308. Low selector 308 compares inputs from temperature controller 310 and transfer function 306a to determine which input is lower and controls steam input, through steam input subsystem 318 into vessel 324, according to the lower input. In this way, low selector 308 can prevent excessive steam usage. For example, if the temperature of the fluid in vessel 324 is very low relative to the desired operational temperature, the temperature controller may require more steam than is available at the highest possible flow rate. Consequently, the low selector will determine that the level output is lower and it will protect the steam flow rate. As a result the fluid level will build up and steam flow will then be increased accordingly. It is understood that a high selector can be used in place of a low selector for connection to a steam input subsystem (with appropriate modification to the other elements of the system).

Water input subsystem 322 is connected to high selector 316. High selector 316 receives two inputs: output from ratio controller 302, which receives input from level controller 304, and modified output from temperature controller 310. As indicated in FIG. 3, temperature controller 310 is configured to act as a direct-acting controller when providing output that is modified by transfer function 306b before being provided as input to high selector 316. As indicated in FIG. 3, level controller 304 is configured to act as a reverse-acting controller when providing input to ratio controller 302 that is provided as input to high selector 316. High selector 316 compares inputs from ratio controller 302 and transfer function 306b to determine which input is higher and controls water flow through water input subsystem 322 into vessel 324 according to the higher input. In certain embodiments, when additional water input is needed to reduce fluid temperature in vessel 324 as indicated by temperature controller 310 exceeding setpoint, high selector control overrides ratio controller 302 and water input is provided to reduce fluid temperature without additionally providing lean amine agent input. If level controller 304 simultaneously determines that fluid level is below setpoint, lean amine agent will flow into vessel 324 until fluid level reaches setpoint independent of ratio controller 302 (i.e., not necessarily in a controlled ratio). Once the high selector is deactivated (e.g., after fluid level reaches a setpoint), ratio controller 302 will be reactivated.

As an example, if the temperature sharply increases then the high selector will obey its input that is based on output of temperature controller 310 to favor water (e.g., reflux water) flow into vessel and consequently inhibit irreversible thermal degradation of the amine agent. In certain embodiments, inert fluid input is significantly cooler than the desired operational temperature of the reclaimer. For example, reflux water may be provided at 120-140° F. As an additional example, if the input received to high selector 316 that is based on the output from level controller 304 is higher than the input received that is based on temperature controller 310, then the level controller input is determined to be higher and water flow through water input subsystem 322 is reduced to prevent a drop in the temperature of fluid in vessel 324. The increased steam supply will then heat up fluid in vessel 324 while lean amine and water flow are minimal (or absent), to allow fluid temperature to reach setpoint. Once the desired operational temperature is reached, additional steam input will stop and system will operate at steady state for a period of time. It is understood that a low selector can be used in place of a high selector for connection to a water input subsystem (e.g., with appropriate modification to the other components of the system).

Water flow through water input subsystem 322 is controlled based on high selector 316 output at the same time that steam flow through steam input subsystem 318 is controlled based on low selector 308 output. As such, water flow and steam flow may be altered simultaneously or nearly simultaneously. The water flow and steam flow do not need to be altered sequentially. Lean amine agent flow through lean amine agent input subsystem 320 can also occur simultaneously.

Transfer functions 306a-b are used manipulate the outputs of the respective level or temperature controller to which they are connected. The transfer functions allow the output of one controller (e.g., level controller 304) to be directly compared to the output of another controller of a different type (e.g., temperature controller 310). Transfer functions can be constant functions or variable functions. In some embodiments, transfer function are determined based on mass and heat balance, which are functions various variables such as composition, heat capacity, temperature, level, and mass flow. In certain embodiments, transfer functions are obtained from a steady state process (e.g., when controller outputs are set as constants). In certain embodiments, the functions are validated through a trial with a steady state condition before being implemented. For example, all controllers in the system could be set up in a manual mode and all selectors could be disconnected in order to determine the transfer functions at steady state. Transfer functions may be determined iteratively (e.g., continuously or discretely). In certain embodiments, other transfer functions in addition to or in place of the transfer functions shown in exemplary reclaimer system 300 may be used in a reclaimer system in order to further manipulate outputs of controllers.

Vessel 324 is a horizontal vessel. In certain embodiments, a horizontal vessel is used. Alternatively, in certain embodiments, a vertical vessel is used. One or more auxiliary vessels may be included in a system in addition to a main reclaiming vessel. In certain embodiments, a vessel is a conventional horizontal kettle reclaimer. Vessels with a range of length to diameter ratios (L/D ratios) can be used. For example, a vessel can have an L/D ratio of between 2 and 5, between 1 and 4, between 2 and 6, less than 5, less than 4, less than 3, or less than 2. Vessel 324 has vapor outlet 326. Water and amine agent vapors form due the elevated temperature of fluid in vessel 324 during an operational cycle and exit through outlet 326. Outlet 326 is located on the top of vessel 324 in order to allow the vapors to naturally escape. One or more other outlets with valves may be disposed on the bottom of a vessel in order to allow residual byproducts to be flushed from the reclaimer at the end of an operational cycle. Such outlets are not shown in FIG. 3. A reclaimer vessel may be operated at a positive pressure or under vacuum or near vacuum conditions. For example, in certain embodiments, a reclaimer is operated at approximately 15 pounds per square inch gauge (psig).

The response of certain embodiments of the present disclosure to various exemplary operational conditions was simulated based on exemplary system 300 in order to observe system behaviors. Certain embodiments of the present disclosure will perform in accordance with the following observations regarding exemplary system 300. The simulated conditions tested dynamic behavior of exemplary system 300 by simulating simultaneous changes in fluid level and fluid temperature at different rates.

a) When the rate of level increase exceeded the rate of temperature decrease (dL/dt>−dT/dt) of fluid in the vessel during the simulation: lean amine agent flow decreased, water flow decreased, and steam flow increased. Furthermore, it was observed that water flow obeyed level controller input to high selector and steam flow obeyed temperature controller input to low selector.

b) When the rate of level increase was exceeded by the rate of temperature decrease (dL/dt<−dT/dt) of fluid in the vessel during the simulation: lean amine agent flow decreased, water flow decreased, and steam flow increased. Furthermore, it was observed that water flow obeyed level controller input to high selector and steam flow obeyed level controller input to low selector.

c) When the rate of level decrease was exceeded by the rate of temperature increase (−dL/dt<dT/dt) of fluid in the vessel during the simulation: lean amine agent flow increased, water flow increased, and steam flow decreased. Furthermore, it was observed that water flow obeyed level controller input to high selector and steam flow obeyed temperature controller input to low selector.

d) When the rate of level decrease exceeded the rate of temperature increase (−dL/dt>dT/dt) of fluid in the vessel during the simulation: lean amine agent flow increased, water flow increased, and steam flow decreased. Furthermore, it was observed that water flow obeyed level controller input to high selector and steam flow obeyed level controller input to low selector.

The behavior of exemplary system 300 during simulation was determined, at least in part, by temperature controller 310 and level controller 304 inputs to high selector 316 and low selector 308 that are connected to fluid input subsystem 322 and steam input subsystem 318, respectively. One or more of the above detailed conditions (i.e., relative rates of change of temperature or level) may be encountered by a reclaimer system in an operational cycle.

In an exemplary use of exemplary reclaimer system 300, reclaimer system 300 is used to reclaim DGA during a sour gas sweetening process. Exemplary reclaimer system 300 is initially filled with fluid comprising lean amine agent until filled to a predetermined level setpoint. System 300 is heated to a desired operational temperature of 360° F., which is used as a temperature setpoint throughout an operational cycle. As the operational cycle proceeds, temperature controller 310 and level controller 304 may sense an increase or decrease in temperature or level above or below their respective setpoints. A deviation in level or temperature of fluid in vessel 324 from their respective setpoints prompts at least one of steam input subsystem 318, water input subsystem 322 and lean amine agent subsystem 320 to alter flow through its subsystem.

High selector 316 controls flow of water through water input subsystem 322 according to the higher input received of the inputs based on the level and the temperature of fluid in vessel 324 while low selector 308 controls flow of steam through steam input subsystem 318 according to the lower input received of the inputs based on the level and the temperature of fluid in vessel 324. For certain first periods in an operational cycle, flow through water input subsystem 322 may be increased or decreased in order to increase or decrease the temperature of the fluid in vessel 324. For certain second periods in an operational cycle not necessarily fully or partially distinct from the certain first periods, flow through steam input subsystem 318 may be increased or decreased in order to increase or decrease the temperature of the fluid in vessel 324. As the level and temperature of fluid in vessel 324 fluctuate during an operational cycle, lean amine agent, water, and steam flow are accordingly altered to maintain the level and temperature at their setpoints. Which input flow is altered and in what way (e.g., higher or lower) is determined by the combination of selectors (316, 308) and controllers (302, 304, 310) as arranged in exemplary reclaimer system 300. For example, lean amine agent and water can be input in their controlled ratio in order to increase a level of fluid in vessel 324 to its setpoint. In certain embodiments, and in this exemplary use, when high selector 316 is activated and water flows through water input subsystem 322, ratio controller 302 is deactivated such that water flows in response to output by high selector 316 without being limited by ratio controller 302. In this exemplary use, lean amine agent is input in a 9:1 ratio relative to reflux water input. Multiple input flows may be altered simultaneously during operation. Operating in this described manner, exemplary system 300 can maintain the temperature of fluid in vessel 324 to between 355° F. and about 365° F. (e.g., between about 358° F. and about 362° F.). The temperature can also be maintained at about 360° F. (e.g., within 0.75%, 0.5%, or 0.2% of 360° F.).

Other Embodiments

Certain embodiments of the present disclosure were described above. It is, however, expressly noted that the present disclosure is not limited to those embodiments, but rather the intention is that additions and modifications to what was expressly described herein are also included within the scope of the disclosure. Moreover, it is to be understood that the features of the various embodiments described herein were not mutually exclusive and can exist in various combinations and permutations, even if such combinations or permutations were not made express herein, without departing from the spirit and scope of the disclosure. In fact, variations, modifications, and other implementations of what was described herein will occur to those of ordinary skill in the art without departing from the spirit and the scope of the disclosure. As such, the disclosure is not to be defined only by the preceding illustrative description. For example, in certain embodiments, reclaimer systems comprise additional elements, subsystems, or controllers other than those described in the preceding text, each of which operate in conjunction with or independent of the temperature and level control mechanisms disclosed herein. For example, a flushing water input subsystem may be included in a reclaimer system in order to assist in cleaning the reclaimer at the end of an operational cycle.

Having described certain implementations of methods and systems for reclaiming amine agents it will now become apparent to one of skill in the art that other implementations incorporating the concepts of the disclosure may be used. Therefore, the disclosure should not be limited to certain implementations, but rather should be limited only by the spirit and scope of the following claims.

What is claimed is:

1. A method for reclaiming one or more amine agents, the method comprising:
    feeding a lean amine agent fluid stream into a reclaimer vessel configured to contain fluid contents, wherein the lean amine agent fluid stream comprises an amine agent and a degradation product;
    indirectly heating the lean amine agent fluid stream added to the reclaimer vessel by feeding a steam stream to the reclaimer vessel;
    feeding an inert fluid stream to into the reclaimer vessel;
    controlling the temperature of the fluid contents within the reclaimer vessel by varying the flow rate of the steam stream to the reclaimer vessel and the inert fluid flow to the reclaimer vessel;
    controlling the level of the fluid contents within the reclaimer vessel, by varying the flow rate of the steam stream to the reclaimer vessel and the inert fluid flow to the reclaimer vessel; and
    withdrawing a vapor stream comprising the amine agent from the reclaimer vessel;
    wherein the degradation product has been formed from a reaction of an amine agent.

2. The method of claim 1, further comprising controlling the temperature of the lean amine agent fluid stream within the reclaimer vessel by varying the flow rate of the lean amine agent fluid stream to the reclaimer vessel.

3. The method of claim 1, further comprising controlling the level of the fluid contents within the reclaimer vessel, by varying the flow rate of the lean amine agent fluid stream to the reclaimer vessel.

4. The method of claim 1, wherein the temperature of the lean amine agent fluid stream within the reclaimer vessel is controlled within a range from 355° F. to 365° F.

5. The method of claim 1, wherein the inert fluid stream comprises water.

6. The method of claim 1, wherein the inert fluid stream comprises reflux water.

7. The method of claim 1, further comprising controlling the ratio of the flowrate of the lean amine agent fluid stream to the flowrate of the inert fluid stream.

8. The method of claim 7, wherein the ratio of the flowrate of the lean amine agent fluid stream to the flowrate of the inert fluid stream is controlled between 3:1 and 10:1.

9. The method of claim 1, wherein the lean amine agent fluid stream comprises at least two amine agents selected from the group consisting of diglycolamine (DGA), monoethanolamine (MEA), diethanolamine (DEA), diisopropanolamine (DIPA), triethanolamine (TEA), methyldiethanolamine (MDEA), 2-amino-2-methyl-1-propanol (AMP), and piperazine (PZ) or a combination thereof.

10. The method of claim 1, wherein the lean amine agent fluid stream comprises at least two degradation products selected from the group consisting of N,N'bis(hydroxyethoxyethyl) urea, morpholine, heat stable salts (HSSs), or a combination thereof.

11. A system for reclaiming one or more amine agents, the system comprising:
    a reclaimer vessel configured to contain a fluid contents;
    a fluid stream inlet configured to feed a lean amine agent fluid stream to the reclaimer vessel, wherein the lean amine agent fluid stream comprises an amine agent and a degradation product;
    a steam stream inlet configured to feed a steam stream to the reclaimer vessel such that the steam stream indirectly heats the fluid contents within the reclaimer vessel;
    an inert fluid stream inlet configured to feed a stream of inert fluid to the reclaimer vessel;
    a temperature controller configured to monitor the temperature of fluid contents and provide input to a high selector and a low selector configured to vary the temperature of the fluid contents, wherein the high selector is configured to vary the temperature of the fluid contents by controlling flow of the inert fluid stream to the reclaimer vessel, and wherein the low selector is configured to vary the temperature of the fluid contents by varying the flow rate of the steam stream to the reclaimer vessel;
    a level controller configured to monitor the level of fluid contents and provide input to the high selector and the low selector, wherein the high selector is configured to vary the level of the fluid contents by controlling flow of the inert fluid stream to the reclaimer vessel, and wherein the low selector is configured to vary the level of the fluid contents by varying the flow rate of the steam stream to the reclaimer vessel;
    and
    a vapor outlet configured to withdraw a vapor stream comprising the amine agent from the reclaimer vessel;
    wherein the degradation product has been formed from a reaction of an amine agent.

12. The system of claim 11, wherein the system is configured to control the temperature of the fluid contents within the reclaimer vessel within a range from 355° F. to 365° F.

13. The system of claim 11, wherein the system is configured to control vary the temperature of the fluid contents by varying the flow rate of the lean amine agent fluid stream to the reclaimer vessel.

14. The system of claim 11, wherein the system is configured to vary the level of the fluid contents within the reclaimer vessel by varying the flow rate of the lean amine agent fluid stream to the reclaimer vessel.

15. The system of claim 11, wherein the reclaimer vessel is a horizontal kettle reclaimer.

16. The system of claim 11, comprising a ratio controller configured to control the ratio between the lean amine agent fluid stream and the inert fluid stream.

17. The system of claim 16, wherein the ratio controller is configured to control a ratio of the flowrate of the lean amine agent fluid stream to the flowrate of the inert fluid stream between 3:1 and 10:1.

18. The system of claim 11, wherein the inert fluid stream comprises water.

19. The system of claim 11, wherein the inert fluid stream comprises reflux water.

20. The system of claim 11, wherein the temperature controller configured to provide input to the high selector and the low selector is configured to provide input to one or more control valves to vary the flow rate of the steam stream to the reclaimer vessel, vary the flow of the inert fluid stream to the reclaimer vessel, and vary the flow rate of the lean amine agent fluid stream to the reclaimer vessel.

21. The system of claim 11, wherein the system comprises a flow rate controller configured to receive one or more inputs based on an output of the high selector or the low selector.

22. The system of claim 11, wherein the system comprises one or more transfer functions, each of the one or more transfer functions modifies an output of the level controller, or the temperature controller and the output of each of the one or more transfer functions is an input of the high selector or the low selector.

* * * * *